United States Patent
Kataoka et al.

US006294614B1

(10) Patent No.: US 6,294,614 B1
(45) Date of Patent: *Sep. 25, 2001

(54) MODIFIED POLYMERS CONTAINING POLY (2-HYDROXYETHYL(METH)ACRYLATE SEGMENT IN THE MOLECULE

(75) Inventors: Kazunori Kataoka, Kashiwa; Masao Kato, Tsukuba; Yukio Nagasaki, Ibaraki; Hotaka Ito, Hakodate; Teiji Tsuruta, Yokohama; Yasuhisa Sakurai, Tokyo; Teruo Okano, Ichikawa; Ken Suzuki, Kawasaki, all of (JP)

(73) Assignee: K. K. Vayu, Nagoya (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/230,535

(22) PCT Filed: Jul. 23, 1997

(86) PCT No.: PCT/JP97/02542

§ 371 Date: Jan. 27, 1999

§ 102(e) Date: Jan. 27, 1999

(87) PCT Pub. No.: WO98/04605

PCT Pub. Date: Feb. 5, 1998

(30) Foreign Application Priority Data

Jul. 29, 1996 (JP) .................................................. 8-214973

(51) Int. Cl.[7] ..................................................... C08F 20/12
(52) U.S. Cl. ............................ 525/242; 525/260; 525/263; 525/283; 525/308; 526/319; 424/450
(58) Field of Search ........................ 525/283, 242, 525/260, 263, 308; 526/319; 424/450

(56) References Cited

U.S. PATENT DOCUMENTS

| 5,130,160 | * | 7/1992 | Goldberg et al. | 427/2 |
| 5,176,975 | | 1/1993 | Kato et al. | 430/49 |
| 5,206,298 | * | 4/1993 | Kawaguchi | 525/283 |
| 5,272,201 | * | 12/1993 | Ma et al. | 524/505 |
| 5,476,509 | | 12/1995 | Keogh et al. | 623/1 |
| 5,545,213 | * | 8/1996 | Keogh et al. | 623/1 |
| 5,631,018 | * | 5/1997 | Zalipsky et al. | 424/450 |

FOREIGN PATENT DOCUMENTS

| 0 480 643 B1 | 5/1996 | (EP) . |
| 50150793 | 12/1975 | (JP) . |
| 58 175553 | 10/1983 | (JP) . |
| 60 031761 | 2/1985 | (JP) . |
| 60 031762 | 2/1985 | (JP) . |
| 60 034451 | 2/1985 | (JP) . |
| 60-31762 | 2/1985 | (JP) . |
| 60 232166 | 11/1985 | (JP) . |
| 61 236831 | 10/1986 | (JP) . |
| 3 223377 | 10/1991 | (JP) . |
| 4 067151 | 3/1992 | (JP) . |
| 4 164908 | 6/1992 | (JP) . |
| 4 264115 | 9/1992 | (JP) . |
| 5 269197 | 10/1993 | (JP) . |
| 6 502782 | 3/1994 | (JP) . |
| 6 136311 | 5/1994 | (JP) . |
| 6 256439 | 9/1994 | (JP) . |
| 7 016291 | 1/1995 | (JP) . |
| 8 507523 | 8/1996 | (JP) . |

* cited by examiner

*Primary Examiner*—David W. Wu
*Assistant Examiner*—Tanya Zalukaeva
(74) *Attorney, Agent, or Firm*—Davis & Bujold, P.L.L.C.

(57) ABSTRACT

Modified polymers containing a poly(2-hydroxyethyl(meth) acrylate) chain as the hydrophilic polymer segment in which a hydrophobic polymer chain or a lipid residue of a sterol is bound to either end of the poly(2-hydroxyethyl(meth) acrylate) chain through a covalent bond or in which the poly(2-hydroxyethyl(meth)acrylate) chain is grafted onto the backbone chain at either end thereof. These modified polymers are excellent in compatibility with liquid or a living body, thus being advantageously usable particularly in medical fields.

12 Claims, No Drawings

MODIFIED POLYMERS CONTAINING POLY(2-HYDROXYETHYL(METH)ACRYLATE SEGMENT IN THE MOLECULE

TECHNICAL FIELD

The present invention relates to a modified polymer containing a poly(2-hydroxyethyl(meth)acrylate) segment in the molecule as a hydrophilic polymer chain and the use thereof, particularly to the use as a medical material.

BACKGROUND ART

Poly(2-hydroxyethyl methacrylate) (hereinafter referred to as polyHEMA in some case) has been evaluated as a polymer which is relatively excellent in biological affinity or biocompatibility, and ABA type block copolymer containing HEMA segment in the molecule is further proposed for a biocompatible medical material (for example, refer to Japanese Patent Application Laid-open No. Sho 55-50028). Moreover, the specific applications of such block copolymer as the medical material, for example, the applications to an artificial blood vessel (Japanese Patent Application Laid-open Nos. Sho 58-175553, 60-31762, 60-34451), a medical suture (Japanese Patent Application Laid-open No. Sho 60-31761), and the like are proposed, and another ABA type block copolymer is also proposed (e.g., Japanese Patent Application Laid-open Nos. Sho 61-236831, 60-232166).

The former group of publications describe the block copolymer in which segment B is a segment derived from polyalkylene oxide having isocyanate groups on opposite terminal ends, and segment A is a segment derived from a)-hydroxyalkyl acrylate. Japanese Patent Application Laid-open No. Sho 61-236831 describes the block copolymer in which segment B is a segment derived from polystyrene having isocyanate groups on opposite terminal ends, and segment A is a segment derived from polyhexyl acrylate.

Moreover, the latter Japanese Patent Application Laid-open No. Sho 60-232166 describes ABA type block copolymer composed of blocks A and B which are both hydrophobic blocks but differ from each other in hydrophobic degree. Additionally, the block A is derived from (meth)acrylic ester having a polyfluoroalkyl group, while the block B contains polystyrene, polybutadiene segments. For these block copolymers, the applications as anticoagulant materials are also proposed.

According to Japanese Patent Application Laid-open No. Sho 55-50028 which belongs to the former group of publications, it is suggested that the block copolymer can form hydrophilic and hydrophobic domains in solution in the state where molecules are getting together, i.e., it can form a micro phase separation structure, so that the biocompatibility can be provided.

As described above, various types of polymers have been developed particularly for medical biocompatible materials, and some of the polymers appear to realize the object of the development to some degree.

However, the conventional material are not necessarily satisfactory for the construction of a blood compatible or biologically compatible surface on various medical devices such as an artificial heart, a dialysis membrane, an artificial lung, a contact lens, a catheter, and the like. Therefore, an object of the present invention is to provide a material superior in blood compatibility or biological compatibility.

DISCLOSURE OF DEVELOPMENT

The present inventors et al. have carried on research under the assumption that if a polymer can be provided in which the mobility of a hydrophilic polymer chain is enhanced separately from the formation of a micro phase separation structure in the solution of a block copolymer (or a copolymer) or the like, a higher resistance may be indicated against the adsorption of, for example, protein in body fluid, platelet in blood, or the like. This is not bound by theory, but if polymer chains having high mobility can be constructed on a certain surface, the adsorption of body fluid components can be expected to be strongly suppressed by the entropy elasticity of the chains as described above.

The present inventors et al. have found that the enlargement of mobility can be achieved by lowering the mobility of either end of the hydrophilic polymer chain by specific means. Specifically, when polyHEMA is used as the hydrophilic polymer chain, by appropriately lowering the mobility of either end thereof, for example, the glass transition temperature (which is, in one view, believed to correspond to the freezing or releasing of polymer chain segment motion or micro-Brownian motion) is remarkably lowered, as compared with a polymer in which such mobility is not lowered. They also found that the strong adsorption suppression against the blood fluid components can be observed as to the polymer.

Therefore, according to the present invention, there is provided a modified polymer containing a poly(2-hydroxyethyl(meth)acrylate) segment as a hydrophilic polymer chain in the molecule, (A) a) one or two said segments being bonded to a hydrophobic polymer chain at either end thereof, b) a plurality of said segments as a graft chain being bonded to a main polymer at either end thereof, or c) said segment being bonded to a bulky lipid residue at either end thereof, and (B) a glass transition temperature being about 45° C. or less.

There is also provided a biologically compatible polymer composition which is prepared from solution or dispersion liquid containing the modified polymer.

There is further provided the use of the modified polymer for manufacturing a biologically compatible polymer composition such as a medical device or apparatus or covering the surface thereof.

DESCRIPTION OF SPECIFIC MODE OF THE INVENTION

The term "(meth)acrylate" for use in the present specification means either methacrylate or acrylate.

The term "medical device or apparatus" for use in the present specification conceptually includes an artificial heart, a dialysis membrane, an artificial lung, an artificial blood vessel, a contact lens, a catheter, and all articles for use in contact with human body fluid or tissue.

The modified polymer of the present invention includes any polymer, as long as it contains a poly(2-hydroxyethyl (meth)acrylate) segment as a hydrophilic polymer chain in the molecule, the mobility of the poly(2-hydroxyethyl(meth) acrylate) segment is significantly strengthened by appropriately suppressing the mobility of either end of the segment, and its glass transition temperature is about 45° C. or less.

A modified polymer is represented as such preferable polymer in general formula (I):

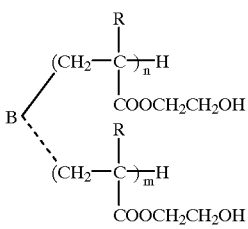

(I)

In the above formula, B denotes a polymer segment derived from either end or both ends living polymer selected from the group consisting of poly(α-methyl-substituted or non-substituted styrene), poly(substituted or non-substituted styrene), polylactide, poly(alkyl(meth)acrylate), poly (dinene) and a living polymer of a copolymer thereof, obtained using an anionic polymerization catalyst, R denotes a hydrogen atom or a methyl group, m and n independently denote a certain integer of 10 to 500, and a broken line denotes that the linked poly(2-hydroxyethyl (meth)acrylate) segment exists or does not exist.

For B, the substituting group in poly(α-methyl substituted or non-substituted styrene) and poly(substituted or non-substituted styrene) may include any group that can be substituted on a benzene ring of styrene and that can achieve the object of the present invention. Examples of the substituting group include $C_{1-6}$ alkyl, e.g., methyl, ethyl; isopropyl halide or silylated $C_{1-6}$ low-class alkyl, e.g., trifluoromethyl, bis (trimethylsilyl)methyl; halogen atom, e.g., chlorine atom, fluorine atom. Additionally, in the present specification, the terms "low-class alkyl" and "C1–6 alkyl" are exchangeably used, and include, for example, methyl, ethyl, n-propyl, iso-propyl, n-butyl, sec-butyl, tert-butyl, n-hexyl, and the like.

In general, the polymer segment with B derived from the both ends living polymer can preferably be obtained using styrene and its derivative as monomers and using Na-naphthalene as the anionic polymerization catalyst. For example, 2-hydroxyethyl(meth)acrylate with a hydroxyl group protected is applied as further monomer to the formed both ends living polymer to continue anionic polymerization reaction. Subsequently, when a protecting group is detached from the hydroxyl group, the modified polymer with poly (2-hydroxyethyl(meth)acrylate) chains applied to the both sides of portion B can be provided. The method is also applied to the manufacture of the modified polymer of the present invention, which has a hydrophobic polymer chain as described later.

It has been heretofore difficult to manufacture a block copolymer in the living anionic polymerization using 2-hydroxyethyl(meth)acrylate as a monomer. However, when 2-hydroxyethyl(meth)acrylate with the hydroxyl group appropriately protected is used as the monomer as described above, a poly(2-hydroxyethyl(meth)acrylate) chain can be formed which has a mobility sufficient to meet the object of the present invention and which has a molecular weight sufficient to provide an adsorption resistance against body fluid components.

Additionally, as the other hydrophobic polymer chain that can constitute the portion B, a chain derived from polylactide, poly($C_{1-20}$alkyl(meth)acrylate), poly(dinene) may be used. Examples of a polymer constituting a typical polymer segment of B including the aforementioned polystyrene group include polystyrene, poly [4-bis (trimethylsilyl)methylstyrene], poly [p-bis(trimethylsilyl) methylisopropenylbenzene]], poly(α-methylstyrene), etc.; poly(lactide) (e.g., polyglycolide, poly(lactic acid), etc.); polyalkyl(meth)acrylate (e.g., polymethyl methacrylate, polyethyl methacrylate, polyisopropyl methacrylate, polydecyl methacrylate, polymethyl acrylate, polyethyl acrylate, polyisopropyl acrylate, etc.); poly(diene) (e.g., polybutadiene, polyisoprene, etc.).

Since the degree of the mobility of the hydrophilic polymer is intrinsically important for the modified polymer of the present invention, the molecular weight of the polymer segment constituting the aforementioned portion B is not limited, but the segment formed of 5 to 100 repeated units is usually preferable.

On the other hand, the molecular weight which can be taken by the poly(2-hydroxyethyl(meth)acrylate) segment or the chain portion is slightly influenced by the type of the hydrophobic polymer chain constituting the portion B, and its optimum value varies, but it is generally in the range of about 1,300 to about 65,000 (in this case, n or m is in the range of about 10 to 500). Additionally, when indicated by n or m, the value is preferably 200 or less, preferably in the range of 50 to 150.

The block copolymer according to the present invention is of ABA type as described above, but the block copolymer of AB type is preferable.

Specifically, the polymer is represented by general formula (I-a):

(I-a)

In the above formula, B' contains repeated units represented by formula:

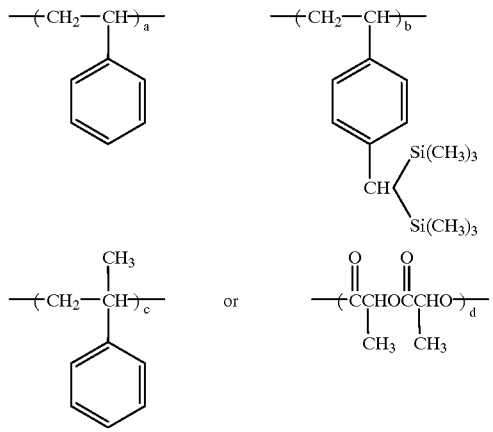

here, a, b, c and d independently denote a certain integer of 5 to 100, and n denotes a certain integer of 10 to 500, preferably 10 to 200, more preferably 50 to 150.

For the ratio of the hydrophilic polymer segment and the hydrophobic polymer segment constituting the block copolymer, the hydrophilic polymer segment needs to occupy a molar ratio of at least 50% by monomer conversion. When the ratio of the hydrophilic polymer segment is 50 mol % or less, the prepared material indicating a sufficient blood or biological compatibility may not be obtained. Additionally, the ratio of the hydrophilic polymer segment is preferably 75 mol % or more, more preferably 80 mol % or more.

The block copolymer having the aforementioned structure dissolves the polymer constituting the hydrophilic polymer chain, but does not substantially dissolve the polymer constituting the hydrophobic polymer chain. When the copolymer is dispersed in the selected solvent, fine micelles having a diameter of several tens of nanometers to several micrometers are formed. Additionally, the micelles form particles around the hydrophobic polymer segment as a core. Furthermore, the particles are conceptually characterized by a structure in which the hydrophilic polymer segment (polyHEMA) is disposed in a brush shape on the surface of the core and by a high mobility. Examples of the selected solvent include dimethylformamide, dimethylacetamide, methanol, ethanol, and aqueous mixture thereof.

The present invention provides another preferable modified polymer, which is represented by general formula (II):

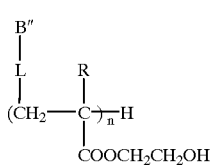

(II)

In the above formula, B' is represented by the following formula:

In the formula, X denotes the repeated unit derived from a monomer selected from the group consisting of α-methyl-substituted or non-substituted styrene, substituted or non-substituted styrene, C1–20 alkyl(meth)acrylate and diene; Y denotes a polymer main chain portion resulting from polymerizable unsaturated bond in which a poly(2-hydroxyethyl (meth)acrylate) segment is covalent-bonded via a continuous group L; p denotes a certain integer of 0 or 5 or more; p and q denote a certain integer of 5 to 500 in total; L denotes a bonding group represented by formula:

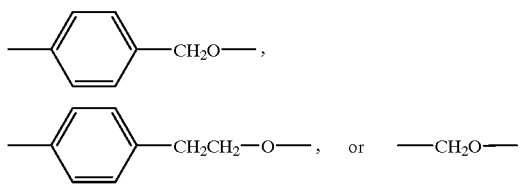

R denotes a hydrogen atom or a methyl group; and n denotes a certain integer of 10 to 500.

As understood from the definition, the repeated unit X means a unit derived from a monomer common with a monomer forming a hydrophobic polymer chain defined as to B in the formula (I), excluding lactide. Therefore, for the substituting group of styrene, alkyl(meth)acrylate, diene, and the like, refer to the description about B of the formula (I).

As can be understood from the aforementioned definition, the repeated unit Y is a unit which can be derived from a macromer. Such macromer has a polymerizable, especially free radical polymerizable unsaturated group on either end of poly(2-hydroxyethyl(meth)acrylate) via a bonding group L. The bonding group L may be any organic group as long as no adverse influence is exerted on radical polymerization, but followings are preferable because the manufacture of macromer is facilitated:

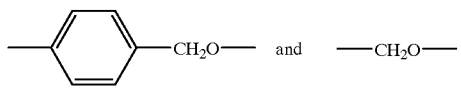

Specifically, Y is especially preferably a repeated unit which can be derived a macromer represented by following formula or a similar macromer:

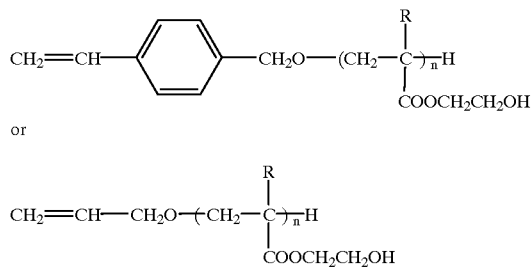

Specifically, the modified polymer represented by the formula (II) can be manufactured preferably from the aforementioned monomer and macromer by known radical copolymerization (p being 1 or more), but may be manufactured from the macromer by homopolymerization (p being 0). In the copolymerization, the ratio of p to q can arbitrarily selected, but it is usually in the range of 5:95 to 95:5, preferably 10:90 to 50:50.

Additionally, the aforementioned macromer can be manufactured by using 4-vinyl benzylic alcohol or allylic alcohol and anionic polymerization catalyst to generate corresponding alkoxide and, subsequently, applying 2-hydroxyethyl (meth)acrylate with the hydroxyl group protected to the system to perform the anionic polymerization reaction.

The present invention provides still further preferable modified polymer, which is represented by general formula (III):

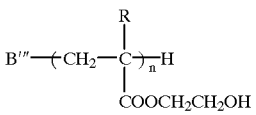

In the formula, B''' denotes a lipid residue selected from a sterol group and covalent-bonded with a poly(2-hydroxyethyl(meth)acrylate) segment via the oxygen atom of a hydroxyl group;

R denotes a hydrogen atom or a methyl group; and n denotes a certain integer of 10 to 500.

The sterol group may be a sterol group chemically synthesized or obtained from natural plant or animal source, or its derivative, as long as the object of the present invention is attained. However, the sterol group which can be obtained from the plant or animal source is preferable for the reason of availability. Examples of sterol group include cholesterol, cholestanol, stigmasterol, 22-dihydro spinasterol, ergosterol, gramisterol, lanosterol, agnosterol, and the like.

The sterol group is commonly classified to a bulky lipid having hydroxyl group in the third position of a steroid skeleton. Therefore, the modified polymer of the formula (III) has a structure in which poly(2-hydroxyethyl(meth) acrylate) is covalent-bonded via the third hydroxyl group. When the modified polymer is manufactured, the aforementioned method of manufacturing the macromer is followed: corresponding alkoxide is generated from the sterol group and the known anionic polymerization catalyst in inactive solvent such as tetrahydrofuran (THF) and the like and, subsequently, 2-hydroxyethyl(meth)acrylate with the hydroxyl group protected is applied to the system to perform the anionic polymerization reaction. The protective group may be detached from the hydroxyl group if necessary.

The modified polymer obtained as described above can be formed into various modes in the same manner as the block copolymer represented by the above formula (I).

In the modified polymer according to the present invention disclosed above, the poly(2-hydroxyethyl(meth) acrylate) chain in the molecule exhibits a high mobility. For example, the glass transition temperature is about 45° C. or less. Additionally, the glass transition temperature is preferably 35° C. or less, more preferably 25° C. as seen from the object of the present invention. For example, polyHEMA obtained by the anionic polymerization of the monomer (ProHEMA) with the hydroxyl group of 2-hydroxyethylmethacrylate (HEMA) being protected and the radical polymerization of HEMA has glass transition temperatures of 80° C. and 50° C., while poly{4-[bis (trimethylsilyl)methylstyrene]-block-(2-hydroxyethylmethacrylate) } (BH10) has a glass transition temperature of 11° C. It is seen that the latter polymer has a significantly low glass transition temperature as compared with the former polymer in which the mobility of either end is not suppressed.

The modified polymer having the low glass transition temperature is remarkably low in adsorptivity of body fluid components such as protein, platelet, and the like, as described later. The modified polymer it provided by the present invention can effectively be used for the manufacture of the medical device for use in contact with body fluid or the like, or used as the composition for covering the surface of the device.

Therefore, according to the present invention, there is provided a biologically compatible polymer composition which is prepared from solution or dispersion liquid containing the modified polymer. When the biologically compatible polymer composition is used in the medical device or the like, it may be combined for use with a material for enhancing the strength of the composition such as plastic, glass, and metal if necessary. For example, the application to artificial hearts, dialysis membranes, artificial lungs, artificial blood vessels, contact lenses, catheters, and the like is strongly intended. Additionally, the composition of the present invention can preferably be used in test tubes, pipettes, and the like which are used for various tests performed by using fluid derived from a human body (body fluid).

The present invention will be described in more detail hereinafter referring to specific examples, which does not mean that the present invention is limited to the examples.

EXAMPLE 1

Manufacture of poly{4-[bis(trimethyl silyl) methylstyrene]-block-(2-hydroxyethylmethacrylate) }

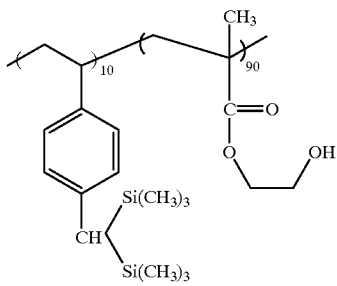

Under −74° C., tetrahydrofuran (THF) was used as solvent, and a monomer or 4-[bis(trimethyl silyl)methyl] styrene (10 mmol) (hereinafter referred to as BSMS) and an initiator or n-butyllithium (1 mmol) were applied with a syringe and reacted for two hours. Thereafter, 1,1-diphenyl ethylene was applied by three times the molar quantity of the initiator with the syringe, and stirring was performed for 30 minutes. Applied to the system was 2-trimethylsilyl oxyethylmethacrylate (90 mmol) (hereinafter referred to as Pro-HEMA) by a dropping funnel, and reaction was performed for one hour. The reaction was stopped by methanol. De-protection was performed by applying the reacted mixture in distilled water to which several drops of 0.1N—HCl was applied. In this manner, the subject block polymer [poly(BSMS)-block-HEMA] or BH10 was quantitatively obtained.

After the obtained block polymer was esterified with acetic anhydride, it was confirmed through measurement by NMR and gel permeation chromatography (GPC) that the molecular weight was about 14,000 (molecular weight distribution=1.1) and the content of BSMS in the polymer was 10 mol %.

EXAMPLE 2

Manufacture of poly(α-methylstyrene-block-HEMA)

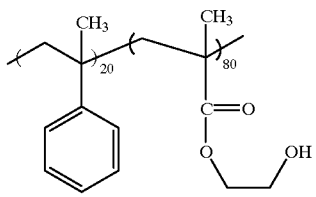

Under −74° C., THF was used as solvent, and a monomer or α-methylstyrene (20 mmol) (hereinafter referred to as (α-MeSt) and an initiator or sec.-butyllithium of catalyst amount were applied with a syringe and reacted for two hours. Thereafter, 1,1-diphenyl ethylene was applied by three times the molar quantity of the initiator with the syringe, and stirring was performed for 30 minutes. Applied to the system was Pro-HEMA (80 mmol) by a dropping funnel, and reaction was performed for one hour. The reaction was stopped by applying methanol. De-protection was performed by applying the reacted mixture in distilled water to which several drops of 0.1N—HCl was applied. The subject block polymer was quantitatively obtained. After the obtained block polymer was esterified with benzoic anhydride, it was confirmed through NMR and GPC measurement that the molecular weight was about 12,000, and the content of α-MeSt in the block polymer was 20 mol %. The block polymer obtained in the example will be abbreviated as MH20 hereinafter.

EXAMPLE 3

Manufacture of poly(lactic acid-block-HEMA)

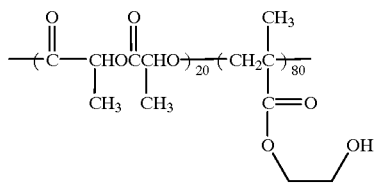

Under 0° C., THF was used as solvent, a monomer or lactide (20 mmol) and an initiator or potassium ethoxide (catalyst amount) were applied to the solvent with a syringe, respectively, and reaction was performed for two hours. The system was cooled to −74° C., pro-HEMA (80 mmol) was applied to the system with a dropping funnel, and reaction was performed for two hours. The reaction was stopped by applying methanol. The subject block polymer was quantitatively obtained. After the obtained block polymer was esterified with benzoic anhydride, it was confirmed through NMR and GPC measurement that the molecular weight was about 13,000, and the content of lactic acid in the block polymer was 20 mol %. The block polymer obtained in the example will be abbreviated as LH20.

EXAMPLE 4

(1) Manufacture of poly(HEMA) macromer

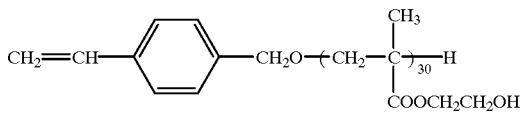

Under −30° C., 4-vinyl benzylic alcohol (5 mmol) and potassium naphthalene (5 mmol) were applied as initiators to a solvent or THF to generate potassium (4-vinyl benzylic alkoxide). Applied to the system was Pro-HEMA (150 mmol), and reaction was performed for 30 minutes. After the reaction, reactive solution was applied to distilled water containing several drops of 0.1NHCl to perform de-protection group reaction. In this manner, the subject macromer was quantitatively obtained. After the obtained macromer was esterified with benzoic anhydride, it was confirmed through analysis by NMR, GPC that the molecular weight was 4,000, and the macromer quantitatively had a vinyl benzylic group on either end.

(2) Manufacture of poly(styrene-graft-HEMA)

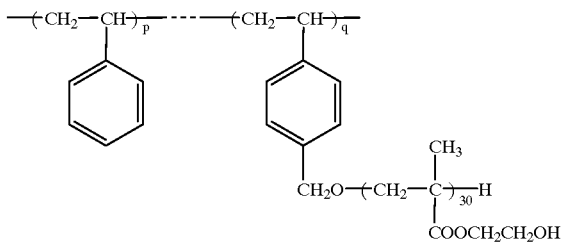

Applied to a glass ampul tube were the poly(HEMA) macromer (15g) obtained in the above (1), styrene (5g), benzene (20 ml) and azobisisobutyronitrile (0.1g). After freezing, deaeration and tube sealing, reaction was performed at 60° C. for 24 hours. The subject polymer was quantitatively obtained by applying the generated material to diethyl ether. After the obtained polymer was esterified with benzoic anhydride, it was confirmed through the analysis by NMR, GPC that the molecular weight of polystyrene/poly (HEMA) was 60,000, and the composition by weight of graft polymer was 75/25. The polymer will be abbreviated as GSH hereinafter.

EXAMPLE 5

Manufacture of cholesterol terminal End Poly (HEMA)

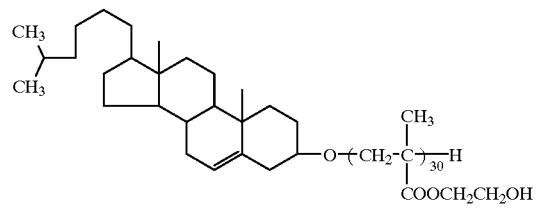

The method described in Example 4(1) was repeated, except that cholesterol (5 mmol) was used instead of 4-vinyl benzylic alcohol. In this manner, the subject polymer quantitatively having cholesterol on the molecular terminal end was obtained by the molecular weight of 4,500. The polymer will be abbreviated as Col-PHEMA below.

TEST EXAMPLE

Glass Transition Temperatures of Various Polymers

Glass transition temperatures were obtained by a differential heat analysis meter to estimate the mobility of poly (HEMA) chains of various polymers. As comparative examples, the glass transition temperatures of polyHEMA having no hydrophobic group on one molecular terminal end, different from the modified polymer of the present invention, and homopolymer constituting a portion other than polyHEMA of the copolymer or the graft polymer of the present invention were obtained in the same manner. Results are shown in following Table 1:

TABLE 1

| SAMPLE | GLASS TRANSITION TEMPERATURE (° C.) |
|---|---|
| (COMPARISON) | |
| POLY (HEMA) (BY ANIONIC POLYMERIZATION OF ProHEMA) | 80 |
| POLY(HEMA) (BY RADICAL POLYMERIZATION) | 50 |
| POLY(BSMS) (BY RADICAL POLYMERIZATION) | 160 |
| POLY(STYRENE) (BY RADICAL POLYMERIZATION) | 100 |
| POLY (α-METHYLSTYRENE) | 130 |
| POLY (LACTIDE) | 45 |
| COMPARATIVE EXAMPLE 1 (FOLLOWING RANDOM COPOLYMER) | 60 |
| (INVENTION) | |
| BH10 (EXAMPLE 1) | 11 |
| MH20 (EXAMPLE 2) | 18 |
| LH20 (EXAMPLE 3) | 20 |
| GSH (EXAMPLE 4) | 9 |
| Col-PHEMA (EXAMPLE 5) | 22 |

It is seen from the table that the modified polymer of the present invention indicates a remarkably lower glass transition temperature (Tg) (has a higher mobility), as compared with the corresponding homopolymer or the like.

EXAMPLE 6

Formation of High-molecular Micelles and Casting Them to Film

The block copolymer (BH10) of 100mg obtained in Example 1 was dispersed in 20 mL of dimethylformamide (DMF). When the dynamic light scattering of the obtained dispersion liquid was measured, it was confirmed that about 100 nm of micelles were formed.

The dispersion liquid was cast onto Teflon to form a film with a thickness of about 100 μm. The in-water equilibrium swelling degree of the film was measured to be about 80%. On the other hand, the in-water equilibrium swelling degree of the film formed by casting the homopolymer (polyHEMA) using dimethylformamide was 30 to 40%.

It is indicated that the cast film obtained from the selective solvent of the block copolymer having the hydrophobic and hydrophilic segments according to the present invention is remarkably richer in moisture content than the cast film obtained from the polymer with only the hydrophilic segment.

It was also confirmed that the contact angle (cos θ) indicating the wettability of BH10film surface was 0.55, which was significantly larger than polyHEMA (θ=0.3).

COMPERATIVE EXAMPLE 1

Random Copolymer of BSMS generated by radical polymerization and HEMA (polyBSMS-co-HEMA):

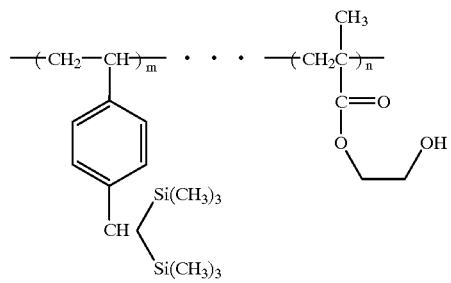

Its dynamic light scattering was measured in the same manner as Example 6, but the formation of high-molecular micelles was not found. A film with a thickness of about 100 μm was formed by casting the solution on Teflon. The in-water equilibrium swelling degree of the film was 25%. On the other hand, the wettability (cos θ) was 0.25.

COMPERATIVE EXAMPLE 2

The block copolymer (BH10) synthesized in Example 1 was dissolved in pyridine as a good solvent of both segments. When the dynamic contact angle and light scattering were measured in the same manner as Example 2, cos θ was 0.28 and no fine particles (high-molecular micelles) were observed.

EXAMPLE 7

Characteristic of BH10 as Surface Treatment

The surface treatment was performed on a glass plate using the aforementioned BH10. For the method, the glass plate was dipped in DMF solution (0.5%) of BH10 (dipping method) to perform coating. The obtained surface and a non-coated glass surface were compared to compare and study platelet adhesion (obtained from the collection ratio of platelet) and activation (obtained by Ca ion level in a cell). As a result, it was confirmed that the surface coated by BH10 was excessively suppressed in the platelet adhesion and activation. For the result, the similar tendency was confirmed from the result of observation of platelet adhering to each surface using an electronic microscope (SEM). Specifically, it can be seen that the glass surface can be provided with a superior blood adaptability by applying the surface treatment to the glass surface with BH10.

(Measurement of Platelet Adhesion)
Preparation of Platelet Floating Liquid

After 10 (volume/volume)% of 3.8% sodium citrate was applied to blood taken from thigh artery of Japanese white hare, platelet-rich-plasma (PRP) was obtained by centrifugal separation (1200 rpm, 20 minutes, 240G). The centrifugal separation was further performed (1500 rpm, 12 minutes, 380G) to obtain a platelet pellet. The pellet was floated again in Hanks buffer liquid containing neither $Ca^{2+}$ nor $Mg^{2+}$. Subsequently, after Fura2-AM of cell membrane transmission type was applied, incubation was performed at 37° C. for 45 minutes to seal Fura2 into a cell. Thereafter, platelet was washed twice to remove Fura2-AM outside the cell, and the platelet concentration was adjusted to 2 to $3\times10^8$ cell/mL. Applied to the system was 2 (weight/weight)% of calcium chloride solution, so that the extracellular calcium concentration was adjusted to 1 mM.

When the platelet floating liquid prepared as described above was brought in contact with the surface with BH10 for ten minutes, 5% of the platelet was adsorbed by the surface.

When glass, polyPHEMA, and polyBSMS surfaces were checked under the same conditions, the adsorption ratios thereof were 50%, 30%, and 40%, respectively.

When the calcium ion concentrations in the platelets not adsorbed under the above conditions were measured, the concentrations for BH10, glass, polyPHEMA, and polyPBSMS were 200 nmol/L, 900 nmol/L, 400 nmol/L, and 700 nmol/L. It was found that the activation of the platelet brought in contact with the BH10 surface was remarkably suppressed.

The aforementioned platelet adhesion was converted from the number of platelets floating in the liquid after contacting the surfaces, which was counted by Coulter Counter (Model 2BI, Coulter Electronics Inc.). On the other hand, the calcium ion concentration was measured in the method described in FEBBS LETTER, 1982, vol. 148, 21 by T. J. Rinks et al.

COMPERATIVE EXAMPLE 3

For the surface of the film cast from pyridine (dissolving both the hydrophilic and hydrophobic segments) solution of BH10 prepared according to the Comparative Example 2, the platelet adhesion and the calcium ion concentration of not-adhering platelet were measured in the same manner as Example 7. As a result, 35% of platelet was adsorbed by the surface, and the calcium ion concentration was 500 nmol/L, indicating a high activation value.

EXAMPLE 8

In the same manner as Example 7, a polystyrene strip, a polyHEMA film, a vinyl chloride plate, and a polymethyl methacrylate (PMMA) plate were dipped, respectively, in DMF solution of BH10 [0.5 (weight/weight)%] for one minute, and dried. The platelet adhesion of each surface and the calcium ion activation were measured.

Results are shown in Table 2 below:

TABLE 2

| | PLATELET ADSORPTION (%) | [Ca$^{++}$] (nmol/L) |
|---|---|---|
| polystyrene | 3 | 150 |
| polyHEMA | 2 | 160 |
| vinyl chloride | 8 | 180 |
| PMMA | 5 | 100 |

It is seen that the blood compatibility of various plastic surfaces is significantly enhanced by the aforementioned treatment in the same manner as the treatment of the glass surface by the prepared material of the block polymer of the present invention.

EXAMPLE 9

The glass surface was treated with dispersion liquids of polymer MH20, LH20, GSH and Col-PHEMA obtained in Examples 2, 3, 4 and 5 in the same manner as Example 6, except that methanol was used as a selective solvent. The particle diameters in the dispersion liquids, platelet adhesions of treated glass surfaces, and calcium concentrations were measured in the method as described above. Results are shown in Table 3 below.

TABLE 3

| | PARTICLE DIAMETER (nm) | PLATELET ADSORPTION (%) | [Ca$^{++}$] (nmol/L) |
|---|---|---|---|
| MH20 | 80 | 4 | 200 |
| LH20 | 120 | 10 | 180 |
| GSH | — | 2 | 100 |
| Col PHEMA | — | 8 | 200 |

INDUSTRIAL APPLICABILITY

According to the present invention, there can be provided a modified polymer composition which can provide various surfaces, especially the surfaces of medical appliances with blood or biological compatibility. For example, when an operation catheter is surface-treated with the composition of the present invention, a high-performance catheter can be prepared. At present, it is substantially impossible to prepare a microfine artificial blood vessel of 6 mm or less, but if the surface of the microfine artificial blood vessel formed of another material is simply coated with the prepared material of the present invention, a microfine artificial blood vessel superior in blood compatibility can be prepared. Such advantage can be prepared especially when the surface of the prepared matter (especially the molded material) is provided with, for example, the significantly reduced platelet adhesion and the blood component activation characteristic. The present invention can thus be used in the field of medical industry.

What is claimed is:

1. A modified polymer containing at least a poly(2-hydroxyethyl(meth)acrylate) segment as a hydrophilic polymer chain in the molecule, (A) the modified polymer being one of; (a) at least one said poly(2-hydroxyethyl(meth)acrylate) segment being bonded to a hydrophobic polymer chain at either end thereof; and (b) a plurality of said poly(2-hydroxyethyl(meth)acrylate) segments as a graft chain being bonded to a main polymer chain at either end thereof;

(B) a glass transition temperature of the modified polymer being about 45° C. or less.

2. A modified polymer containing at least a poly(2-hydroxyethyl(meth)acrylate) segment as a hydrophilic polymer chain in the molecule, (A) the modified polymer being one of; (a) at least one of a first and second poly (2-hydroxyethyl(meth)acrylate) segment being bonded to a hydrophobic polymer chain at either end thereof, (b) a plurality of said poly(2-hydroxyethyl(meth)acrylate) segments as a graft chain being bonded to a main polymer chain at either end thereof; and (c) said segment being bonded to a bulky lipid residue at either end thereof, (B) a glass transition temperature of the modified polymer being about 45° C. or less; the modified polymer represented in general formula (I):

(I)

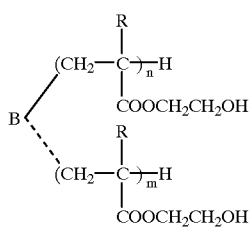

in said formula, B denoting a polymer segment derived from either end of both ends living polymer selected from the group consisting of poly(α-methyl-substituted or non-substituted styrene), poly(substituted or non-substituted styrene), polylactide, poly(alkyl(meth) acrylate), poly(dinene) and a living polymer of a copolymer thereof, obtained using an anionic polymerization catalyst, R denoting a hydrogen atom or a methyl group, m and n independently denoting a certain integer of 10 to 500, and a broken line denoting that the linked poly(2-hydroxyethyl(meth)acrylate) segment exists or does not exist.

3. The modified polymer according to claim 1 represented by general formula (I-a):

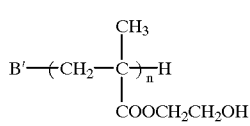
(I-a)

in said formula, B' denoting the segment derived from anionic living polymerization and containing repeated units represented by formula selected from the group:

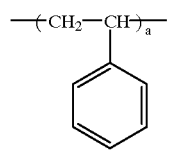   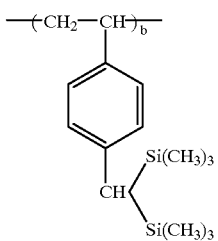

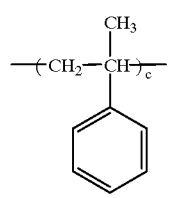   and   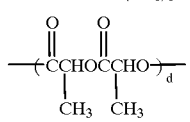

a, b, c and d independently denoting a certain integer of 5 to 100, and n denoting a certain integer of 10 to 500.

4. The modified polymer according to claim 1 represented by general formula (II):

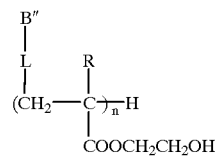
(II)

in said formula, B" being represented by formula:

in the formula, X denoting a repeated unit derived from a monomer selected from the group consisting of α-methyl-substituted or non-substituted styrene, substituted or non-substituted styrene, $C_{1-20}$alkyl(meth) acrylate and diene; Y denoting a polymer main chain portion resulting from polymerizable unsaturated bond in which the poly(2-hydroxyethyl(meth)acrylate) segment is covalent-bonded via a continuous group L; p denoteing a certain integer of 0 or 5 or more; p and q denoting a certain integer of 5 to 500 in total;

L denoting a bonding group represented by formula:

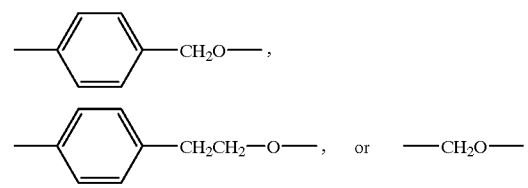

R denoting a hydrogen atom or a methyl group; and n denoting a certain integer of 10 to 500.

5. The modified polymer according to claim 4 wherein X is represented by formula:

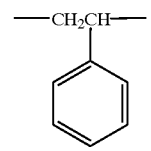

and Y-L is represented by formula:

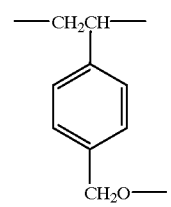

6. The modified polymer according to claim 1 represented by general formula (III):

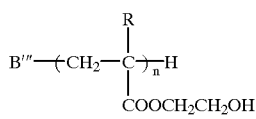
(III)

in said formula, B''' selected from a sterol group and covalent-bonded with the poly(2-hydroxyethyl(meth)acrylate) segment via the oxygen atom of a hydroxyl group;

R denoting a hydrogen atom or a methyl group; and n denoting a certain integer of 10 to 500.

7. The modified polymer according to claim 6 wherein the sterol group is obtained from an animal or plant source.

8. A biologically compatible polymer composition prepared from a solution or a dispersion liquid which contains the modified polymer claimed in claim 1.

9. The biologically compatible polymer composition according to claim 8 wherein a solvent dissolves a polymer formed of the poly(2-hydroxyethyl(meth)acrylate) segment, but does not dissolve a polymer formed of a hydrophobic polymer segment.

10. A polymer composition containing the modified polymer claimed in claim 1 for providing a surface of a medical device or appliance with blood or biological compatibility.

11. A modified polymer containing at least a poly(2-hydroxyethyl(meth)acrylate) segment as a hydrophilic polymer chain in the molecule, (a) the modified polymer being one of: (a) at least one said poly(2-hydroxyethyl(meth)acrylate) segment being bonded to a hydrophobic polymer chain at either end thereof; and (b) a plurality of said poly(2-hydroxyethyl(meth)acrylate) segments as a graft chain being bonded to a main polymer chain at either end thereof; and (b) a glass transition temperature of the modified polymer being about 45° C. or less;

(c) wherein the at least one said poly(2-hydroxyethyl(meth)acrylate) segment modified polymer and the plurality of said poly(2-hydroxyethyl(meth)acrylate) segments as a graft chain are not bonded to a lipid residue at either end thereof.

12. A modified polymer containing at least a poly(2-hydroxyethyl(meth)acrylate) segment as a hydrophilic polymer chain in the molecule, (a) the modified polymer being one of: (a) at least one said poly(2-hydroxyethyl(meth)acrylate) segment being bonded to a hydrophobic polymer chain, other than a lipid residue, at either end thereof; and (b) a plurality of said poly(2-hydroxyethyl(meth)acrylate) segments as a graft chain being bonded to a main polymer chain, other than a lipid residue, at either end thereof;

(b) a glass transition temperature of the modified polymer being about 45° C. or less;

(c) wherein the at least one said poly(2-hydroxyethyl(meth)acrylate) segment modified polymer and the plurality of said poly(2-hydroxyethyl(meth)acrylate) segments as a graft chain, are bonded directly to one of the hydrophobic polymer chain, and the main polymer chain, other than a lipid residue.

* * * * *